(12) United States Patent
Chung

(10) Patent No.: US 7,939,255 B2
(45) Date of Patent: May 10, 2011

(54) DIAGNOSTIC METHODS FOR COLORECTAL CANCER

(75) Inventor: Yeun-Jun Chung, Seoul (KR)

(73) Assignee: Catholic University Industry Academy Cooperation Foundation, Seoul (KR)

( * ) Notice: Subject to any disclaimer, the term of this patent is extended or adjusted under 35 U.S.C. 154(b) by 62 days.

(21) Appl. No.: 11/824,896

(22) Filed: Jul. 3, 2007

(65) Prior Publication Data

US 2008/0096205 A1 Apr. 24, 2008

Related U.S. Application Data

(60) Provisional application No. 60/864,413, filed on Nov. 6, 2006.

(30) Foreign Application Priority Data

Jul. 3, 2006 (KR) .......................... 10-2006-0061741

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6; 435/91.2; 435/91.21; 536/23.5

(58) Field of Classification Search .......................... None
See application file for complete search history.

(56) References Cited

U.S. PATENT DOCUMENTS

2001/0018183 A1* 8/2001 Bao et al. .......................... 435/6

OTHER PUBLICATIONS

Kim et al. Gastroenterology. 2006. 131: 1913-1924, published online Oct. 18, 2006.*
Barbashina et al. Clinical Cancer Research. Feb. 2005. 11: 1119-1128.*
Henrich et al. Clinical Cancer Research. Jan. 1, 2006. 12(1): 131-138.*
Ogunbiyi et al. Gastroenterology. 1997. 113: 761-766.*
Liu et al. Clinical Immunology. 2004. 112: 225-230.*
Coleman. Drug Discovery Today. 2003. 8: 233-235.*
Saetre et al. Molecular Brain Research. 2004. 126: 198-206.*
Maris et al. Journal Clinical Oncology. 2000. 18: 1888-1899.*

* cited by examiner

*Primary Examiner* — Carla Myers
(74) *Attorney, Agent, or Firm* — Edwards Angell Palmer & Dodge LLP; Kongsik Kim

(57) ABSTRACT

The present application discloses a diagnostic method and a kit for prognosis assessment of colorectal cancer (CRC) and a novel tumor suppressor gene to be used for diagnosis of colorectal cancer (CRC), the method comprising the steps of: (a) identifying recurrently altered regions (RAR) on a chromosome; and (b) detecting genomic alterations in the RAR. The present method makes it possible to perform early diagnosis as well as prognosis assessment for various cancers and tumors including colorectal cancer (CRC).

2 Claims, 11 Drawing Sheets

DIAGNOSTIC METHODS FOR COLORECTAL CANCER

RELATED APPLICATIONS/PATENTS & INCORPORATION BY REFERENCE

The present application claims the benefit of Korean Patent Application No. 10-2006-0061741 filed Jul. 3, 2006 and U.S. Provisional Application No. 60/864,413 filed Nov. 6, 2006, the entire contents of which are hereby incorporated by reference.

Also, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

BACKGROUND

1. Technical Field

The present invention relates to novel diagnostic methods and kits for colorectal cancer (CRC). More specifically, the present invention relates to diagnostic methods, comprising the steps of; a) identifying recurrently altered regions (RAR) on chromosome; and (b) detecting genomic alterations in RAR.

Also the present invention relates to kits for prognosis assessment of colorectal cancer (CRC) and novel tumor suppressor genes for diagnosis of colorectal cancer (CRC).

2. Background Art

Colorectal cancer (CRC) accounted for about 1 million new cases in 2002 worldwide (9.4% of the world total). In terms of incidence, CRC ranks fourth in men and third in women. Mortality is about one half of incidence (about 529,000 deaths in 2002), while prevalence is second only to that of breast cancer worldwide, with an estimated 2.8 million persons alive with CRC diagnosed within 5 years of diagnosis. There is at least a 25-fold variation in occurrence of CRC worldwide. The incidence rates are highest in developed countries, while they tend to be low in Africa and Asia. In Korea, CRC cancer became the fourth leading cause of cancer death in 2004 and the age-standardized incidence rates of CRC in both sexes are higher than world average rates. These geographic differences are probably due to genetic background as well as environmental factors since CRC is one of multifactorial diseases; environmental and genetic factors interact and may work synergistically to develop a disease.

It is known that multiple mutations accumulate during the pathogenesis of CRC. Two major forms of genetic instability in CRC have been classified as either microsatellite instability (MIN) or chromosomal instability (CIN). In about 13% of CRC, mismatch repair deficiency leads to MIN, whereas in the remaining 87%, CIN appears to result in gains and losses of genetic materials. So, characterization of CIN may help to identify potential oncogenes and/or tumor suppressor genes and furthermore elucidate the pathogenesis of CRC.

To characterize CIN, conventional comparative genomic hybridization (CGH) has been used to identify multiple chromosomal imbalances in a sample from a single experiment. However, resolution of the conventional CGH is insufficient for precise identification of sub-microscopic changes. As accumulated evidence suggests that changes in genomic dosage contribute to tumorigenesis by altering the expression levels of cancer-related genes, more detailed analyses with high resolution are necessary.

There is thus a need for an improved diagnostic method.

The information disclosed in this Background section is only for enhancement of understanding of the background of the invention and should not be taken as an acknowledgement or any form of suggestion that this information forms the prior art that is already known to a person skilled in the art.

SUMMARY OF THE INVENTION

The present invention has been made in an effort to provide a new diagnostic method and a kit for prognostic assessment of colorectal cancer. The present invention has been made based, at least in part, on the following discovery. To see genomic alterations and their clinicopatholigical implications in CRC, the present inventor applied genome-wide array CGH to the genomic DNAs extracted from microdissected tissues of 59 colorectal cancer cases. Using this strategy, various genomic copy number changes related to CRC including novel recurrently altered regions (RAR) were identified and associations between genetic alterations detected by array CGH and clinicopathological variables were examined.

As a result, twenty-seven RARs were identified in CRC and RAR-L1 and RAR-L20 found to be independent indicators of poor prognosis. Expression of CAMTA1, located in RAR-L1, was frequently reduced in CRCs and low CAMTA1 expression was significantly associated with poor prognosis, which indicates CAMTA1 plays as a tumor suppressor in CRC.

The present invention is broadly directed to a method for prognosis assessment of colorectal cancer (CRC) by identifying recurrently altered genomic regions (RAR) in colorectal cancer with high resolution (one Mb-resolution) microarray based comparative genomic hybridization (array CGH), and using the specific recurrently altered genomic regions in colorectal cancer as a prognostic marker for colorectal cancer progress.

In one aspect, the present invention provides a diagnostic method for prognostic assessment of colorectal cancer, comprising the steps of: (a) obtaining a nucleic acid sample from a subject; (b) identifying recurrently altered regions (RAR) on chromosome by array CGH; (C) detecting variation of expression of a specific gene in the RAR; and (d) performing prognostic assessment based on the detected variation.

In a preferred embodiment, the RAR in the step (b) may be one or more region selected from group consisting of RAR-L1 (loss of chromosome 1p36) and RAR-L20 (loss of chromosome 21q22). Preferably, the specific gene in the step (c) may be a cancer suppressor gene located in the RAR. More preferably, the cancer suppressor gene may be CAMTA1. When reduced gene expression level of CAMTA1 is detected, it may be assessed as poor prognosis.

In another aspect, the present invention provides a diagnostic kit for prognostic assessment of colorectal cancer, which comprises: (a) an array CGH instrument for identifying recurrently altered regions (RAR) on a chromosome; and (b) an image analysis device for detecting variation of expression of a specific gene in the RAR. The kit may further include a container for holding the instrument and device.

In still another aspect, the present invention provides a use of cancer suppressor gene CAMTA1 for prognostic assessment of colorectal cancer.

DETAILED DESCRIPTION

Figure 1:
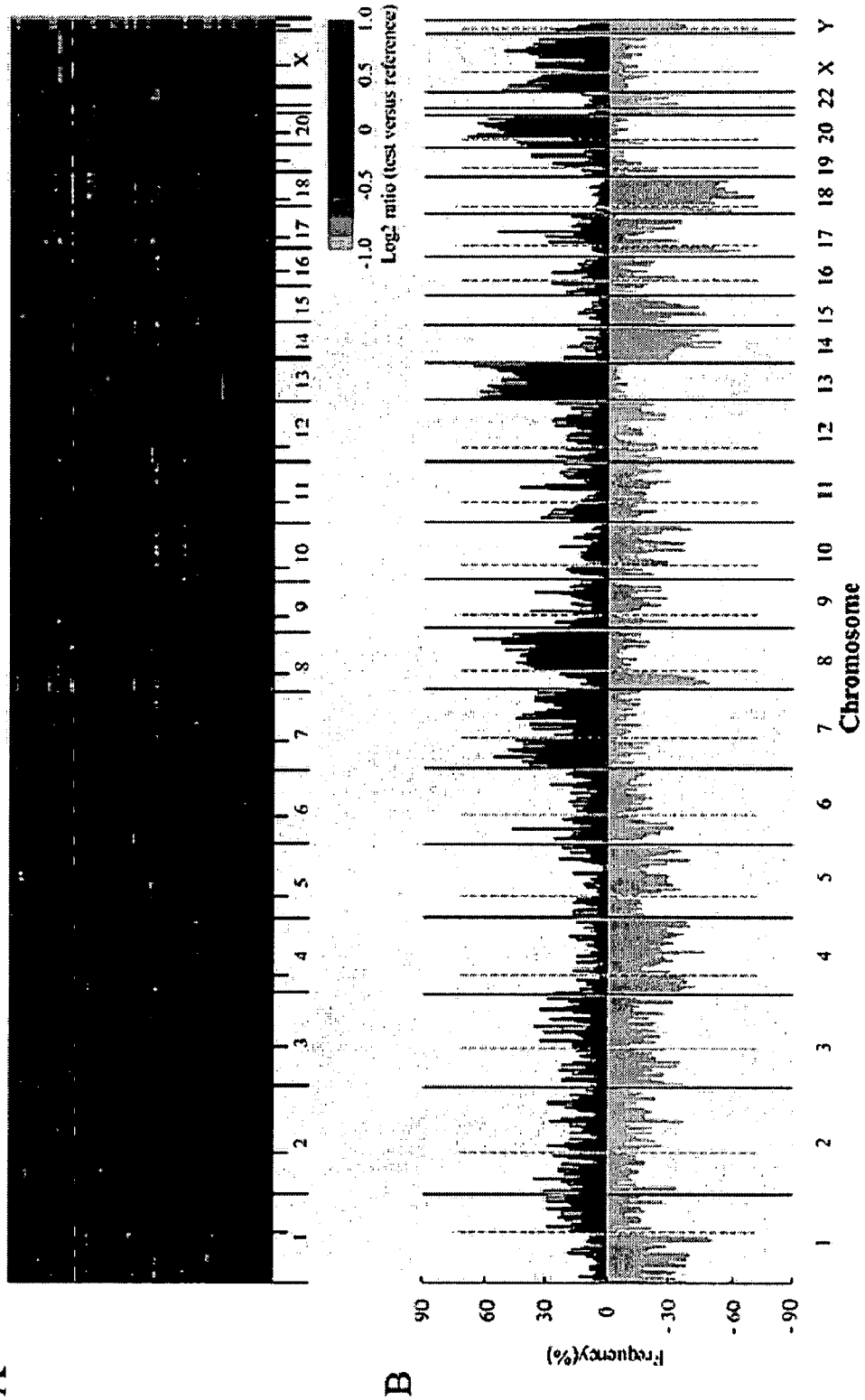
FIG. 1 shows an analysis result for genome of patients with colorectal cancer. A: Genome-wide profiles of patients with colorectal cancer, B: Frequencies of all significant gains and losses on chromosome

Hereinafter, the present invention will be described in further detail with reference to examples. It is to be understood, however, that these examples are for illustrative purposes only and are not to be construed to limit the scope of the present invention.

Example 1

General Characteristics of Genomic Alterations in Colorectal Cancer (1) Collection of Tissue Samples from Patients with Colorectal Cancer Surgical specimens from 59 CRC patients, who underwent surgical resection during 1995 and 1997 at Dankook University Hospital, Cheonan, Korea, were examined in this invention. This examination was performed under the approval of Institutional Review Boards of Kangnam St. Mary's Hospital, The Catholic University of Korea, Korea. After surgical resection, tumor and adjacent normal tissues from each patient were collected separately and snap frozen in deep freezer. Frozen sections were prepared of 10 µm thickness on a gelatin coated slide using cryotom (Reighert-Jung, Germany). After H&E staining of frozen section, tumor cell rich area (more than 60% of tumor cells) and normal cell area were selected under the microscope and dissected manually. Microdissected tissues were transferred into the cell lysis buffer (1% proteinase-K in TE buffer) and genomic DNA was extracted by incubating at 50° C. for 12 hours. DNA from normal tissue was used as reference for array CGH. Extracted DNA was purified using a DNA purification Kit (Solgent, Daejon, Korea) and quantified using NanoDrop ND-1000 spectrophotometer (NanoDrop Technologies, Delaware USA). Histopathological review of the tumors was performed by experienced pathologist according to the standard TNM classification in the American Joint Committee on Cancer guidelines.

(2) Array Comparative Genomic Hybridization and Data Processing

We used human large-insert clone arrays with 1 Mb resolution across the whole genome printed by the Sanger Institute Microarray Facility (Fiegler et al, Genes Chromosomes Cancer 2003; 36:361-374; Kim T M et al, Clin Cancer Res 2005; 11:8235-8242.) Details of DNA labeling, pre-hybridization, hybridization, and post-hybridization processes are described below. Genomic DNA from cancer tissue was labeled with Cy3-dCTP and DNA from normal tissue of the same patient was labeled with Cy5-dCTP. Open-well hybridization was done as described previously. Arrays were scanned using GenePix 4100A scanner (Axon Instruments, USA) and the image was processed using GenePix Pro 6.0. Normalization and re-aligning of raw array CGH data were performed using the web-based array CGH analysis interface, ArrayCyGHt (URL: genomics.catholic.ac.kr/arrayCGH/). In brief, we used print-tip loess normalization method for analysis. Mapping of large insert clones was done according to the genomic location in the Ensembl and UCSC genome browser. In sum, 2,981 BAC clones out of initial 3,014 clones were processed. Information of whole clone set is available in the Ensembl human genome browser (URL: ensembl.org/Homo_ sapiens/index.html).

(3) Data Analysis for Chromosomal Alterations

To set the cutoff value for chromosomal alterations of individual clones, we performed four independent series of normal hybridization (three self to self and one male to female hybridizations) as controls. Based on the control hybridizations, the cutoff value for copy number aberration was set to above or below 3-fold of standard deviation at individual data point. Regional copy number change was defined as DNA copy number alterations stretching across more than 2 consecutive BAC clones, but not across entire chromosomes. High-level amplification of clones was defined when their intensity ratios were higher than 1.0 in log 2 scale, and vice versa for homozygous deletion. The boundary of the copy number changes was assigned to the halfway between two neighboring clones. RAR was defined as regional copy number changes, which appear in at least 10 tumor samples.

(4) The Data of Genomic Alterations

The clinicopathological data of all 59 patients are summarized in Table 1. There were 39 men and 20 women and the mean patient age at the time of surgery was 58.7 years (range from 23 to 81). Among the 59 cases, 41 patients (69.5%) had rectosigmoid cancer. Thirty six cancers (61.0%) were categorized as early stage tumors. At the end of the follow up, 23 patients were dead.

TABLE 1

| General characteristics of study subjects | |
| --- | --- |
| Number of patients | 59 (100%) |
| male | 39 (66.1%) |
| female | 20 (33.9%) |
| Age group | |
| Male | 59.2 |
| Female | 57.8 |
| <60 | 31 (52.5%) |
| >=60 | 28 (47.5%) |
| Stage | |
| Early (Satge I and II) | 36 (61.0%) |
| Advanced (Stage III and IV) | 23 (39.0%) |
| Tumor site | |
| Rectosigmoid | 41 (69.5%) |
| Other sites | 18 (30.5%) |

Note:
other sites denote ascending, transverse, descending colon and cecum

The overall genomic alterations detected in 59 colorectal cancers are illustrated in FIG. 1A. The frequency plot of the chromosomal changes shows that they are not randomly distributed, but clustered in several hot regions across the whole genome (FIG. 1B). The array CGH signal intensity ratio (log 2 scale) data of the 59 cases can be downloaded from our website (URL: lib.cuk.ac.kr/micro/CGH/colon.htm).

The mean number of altered clones per case was 764.8 out of total 2,981 clones (range from 58 to 1,540). The mean numbers of altered clones are significantly higher in males (832.6 vs. 632.6, p=0.04), advanced stage group (897.7 vs. 679.9, p=0.03), and rectosigmoid cancer (826.7 vs. 623.8, p=0.03). The most frequent changes of entire chromosomal arms were gains of 13q (31/59, 52.5%), 20q (30/59, 50.8%), 20p (23/59, 40.0%), 7p (21/59, 35.6%), 8q (20/59, 33.9%) as well as losses of 18q (29/59, 49.2%), 18p (27/59, 45.8%) and 17p (26/59, 44.1%).

Example 2

Verification of Copy Number Alterations

To verify the copy number changes identified, multiplex ligation-dependent probe amplification (MLPA) analysis was performed using MLPA-Aneuploidy test kit P095 (MRC Holland, Amsterdam, Netherlands) as described below. Briefly, genomic DNA (250 ng) was denatured for 10 minutes at 98° C. and 3 μl of probe-mix including buffer was added. Then the mixture was heated at 95° C. for 1 minute and incubated at 60° C. for 16 hours. Ligation reaction was performed using a heat stable ligase-65 enzyme at 54° C. for 15 minutes. Ten μl of ligation reaction was mixed with 40 μl of PCR reaction mix containing universal primers. One primer is unlabelled and the other is labeled with FAM [N-(3-fluoranthyl)maleimide]. The thermal cycling was as follows: 1 minute at 95° C. followed by 35 cycles of 30 sec at 95° C., 30 sec at 60° C., and 60 sec at 72° C. Analysis of the amplified fragments was performed using ABI PRISM 3730 XL DNA Analyzer (Applied Biosystems, Foster City, USA) with ROX-500 (ROX-500 Genescan, ABI, USA) as a size standard. The peak area of the PCR products was determined by Genotyper software (Applied Biosystems, Foster City, USA) and data analysis was performed using a simplified analysis method from Coffalyser macro (URL: mlpa.com).

Figure 2A:
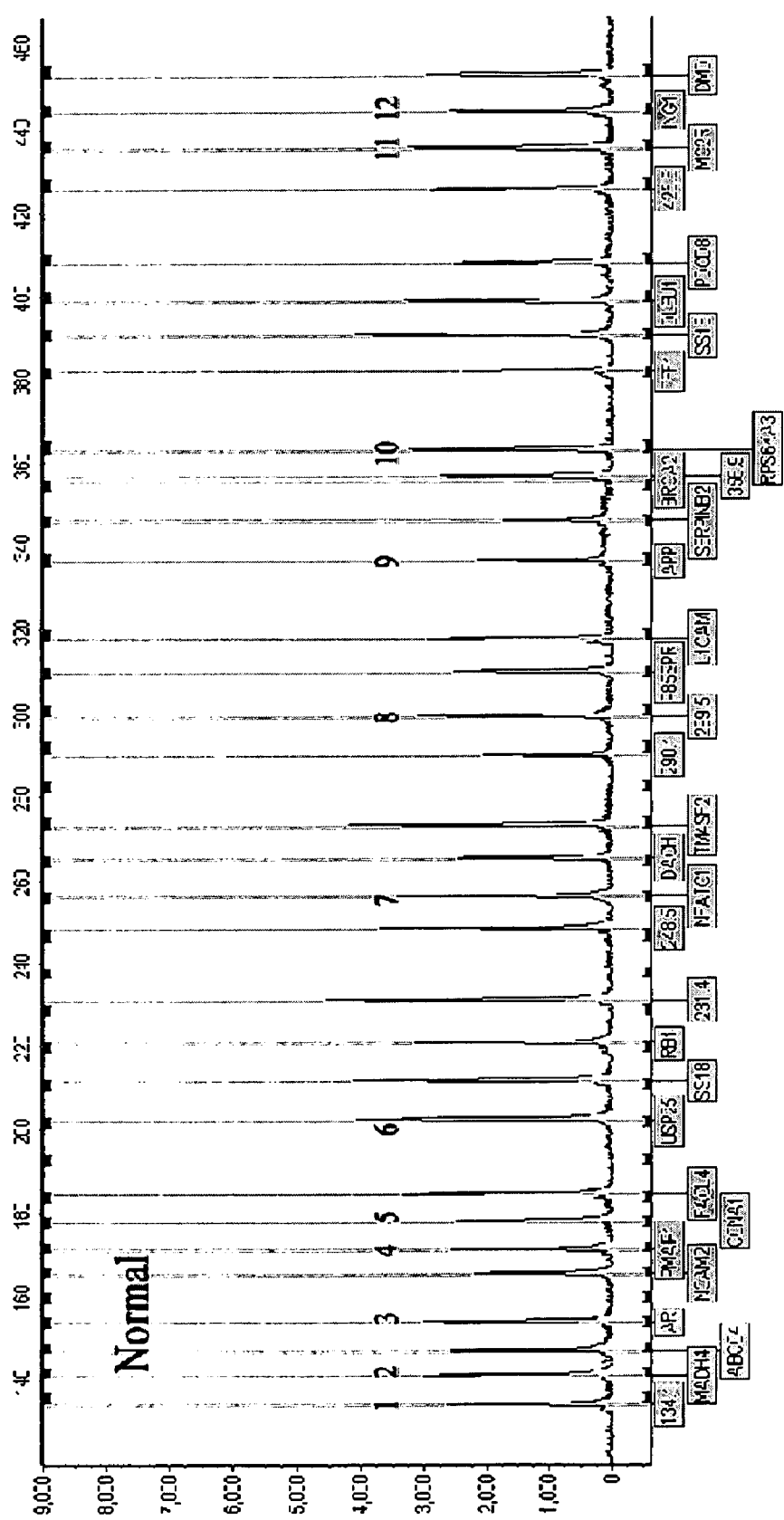
FIG. 2 shows an analysis result for verification of array-CGH copy number profiles. A: normal tissue DNA, B: tumor tissue DNA of CCRC80, C: tumor versus normal peak ratio plot
Figure 2B:
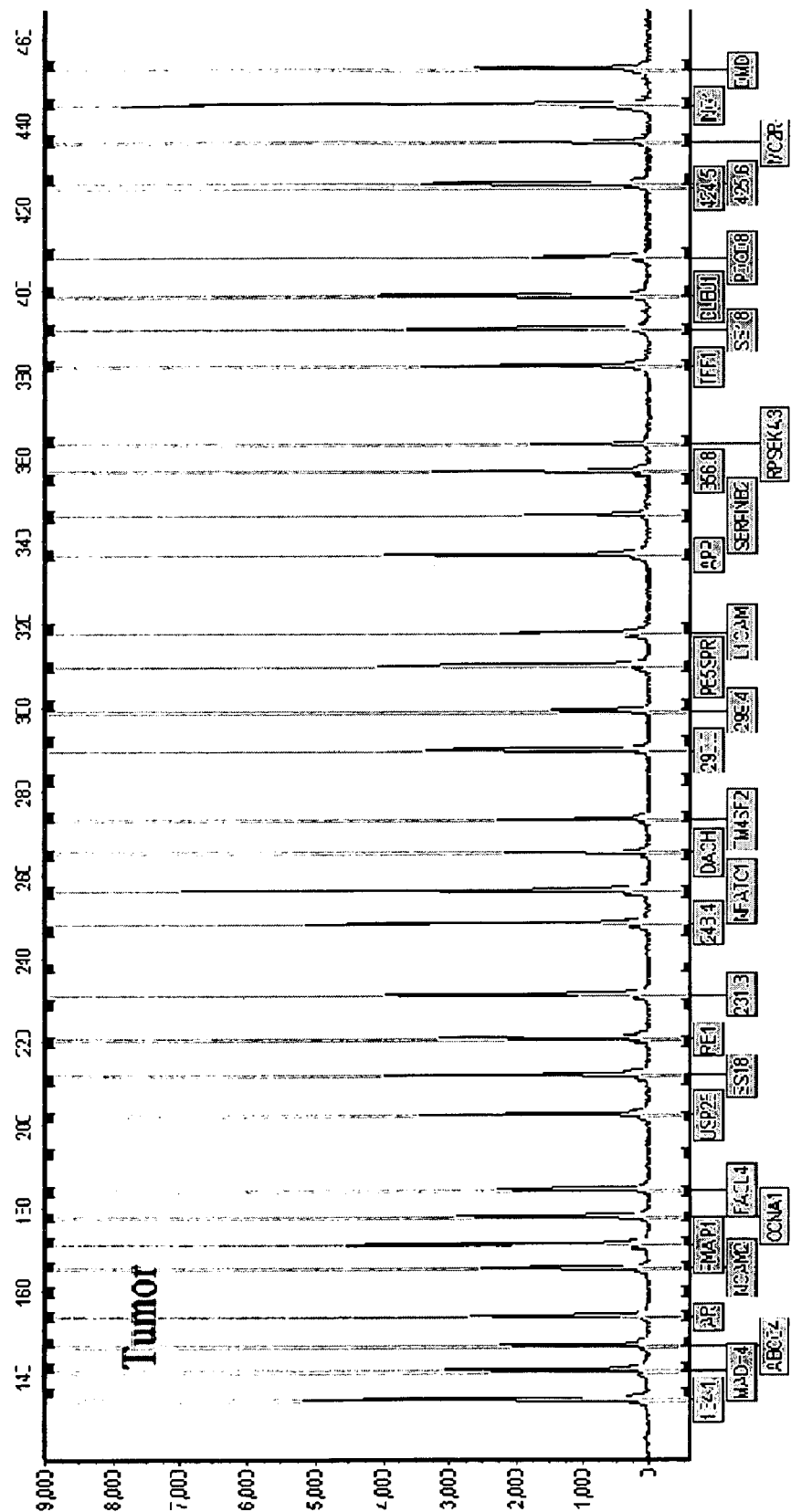
Figure 2C:
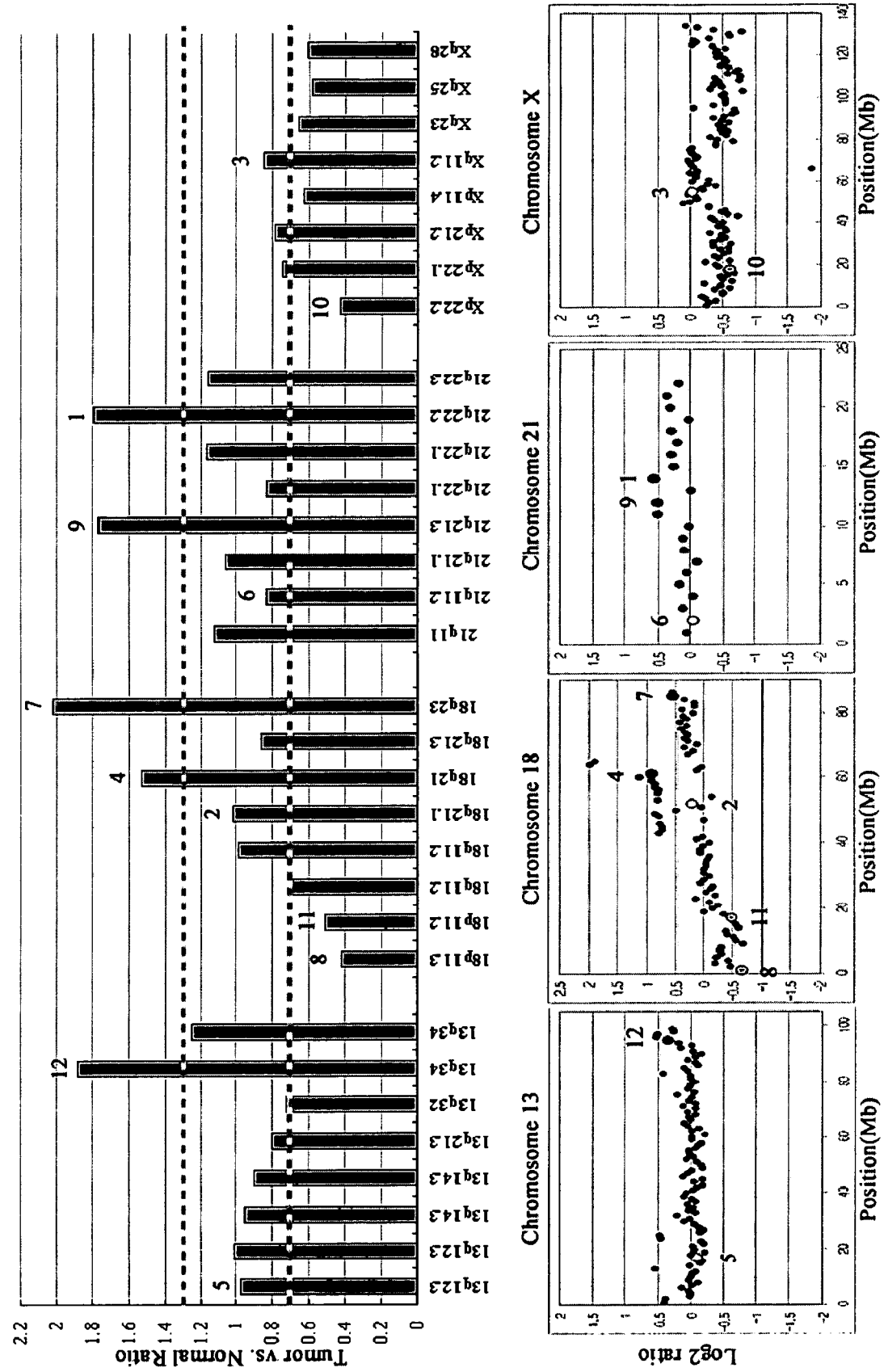

To verify the copy number changes identified by array-CGH, we performed MLPA analysis with 13 primary CRCs showing copy number aberrations. Copy number alterations identified by array-CGH were generally consistent with MLPA results. FIG. 2 illustrates example of MLPA validation results. Twelve peaks (numbered at each peak) are the examples of copy number alterations on chromosome 13, 18, 21, and X.

Example 3

Recurrently Altered Regions

In addition to the entire chromosomal changes, a lot of regional copy number changes were identified. Among those regional changes, we defined the chromosomal region recurrently altered in at least 10 cases as RAR. In sum, 7 RAR gains (RAR-G) and 20 RAR losses (RAR-L) were detected. Table 2 lists the map position, size and cancer-related genes located in 27 RARs. Five RARs were detected in more than 40% of cases; RAR-G4 (28/59, 47.5%), RAR-L2 (27/59, 45.8%), RAR-L5 (25/59, 42.4%), RAR-L14 (28/59, 47.5%), and RAR-L17 (28/59, 47.5%) (Table 2).

TABLE 2

Recurrent genetic alteration regions in 59 colorectal cancers

| | Alterations | BAC clone ID | Cytoband | Boundary (Mb) | Size (Mb) | Frequency | Putative cancer related genes |
|---|---|---|---|---|---|---|---|
| Gain | RAR-G1 | RP11-440P5-RP11-373L24 | 2p16.1-p15 | 59.90-61.92 | 2.01 | 15/59 | BCL11A, REL |
| | RAR-G2 | RP11-163H6-RP11-4S4D1S | 3q26.2-q26.32 | 172.14-178.64 | 6.49 | 12/59 | PLD1, ECT2, |
| | RAR-G3 | RP11-196O16-RP11-486P11 | 7p21.1 | 15.35-20.32 | 4.97 | 21/59 | AGR2, TWIST1 |
| | RAR-G4 | RP11-495D4-RP11-17E16 | 8q24.13-q24.21 | 126.22-131.11 | 4.88 | 28/59 | MYC |
| | RAR-G5 | RP11-121C18-RP11-34N19 | 11p15.1-p14.3 | 20.97-23.47 | 2.49 | 11/59 | |
| | RAR-G6 | RP11-31I23-RP1-68D18 | 11p13 | 34.47-35.49 | 1.01 | 19/59 | CD44 |
| | RAR-G7 | RP3-404F18-RP3-394F12 | Xq24-q25 | 117.92-125.02 | 7.10 | 21/59 | BIRC4 |
| Loss | RAR-L1 | RP3-438L4-RP11-338N10 | 1p36.31-p36.23 | 6.52-8.43 | 1.90 | 15/59 | CAMTA1 |
| | RAR-L2 | RP11-428D12-RP1-86A18 | 1p33-p32.3 | 48.50-51.17 | 2.66 | 27/59 | FAF1 |
| | RAR-L3 | RP5-944F13-RP11-175G14 | 1p31.1 | 69.56-72.27 | 2.70 | 15/59 | CTH, PTGER3 |
| | RAR-L4 | RP5-963M5-RP4-739M21 | 1p31.1 | 76.26-77.47 | 1.20 | 23/59 | |
| | RAR-L5 | RP11-22A3-RP11-446J8 | 4p15.33-p15.32 | 12.05-17.17 | 5.11 | 25/59 | |
| | RAR-L6 | RP11-100N21-RP11-415L23 | 4p12 | 46.67-48.32 | 1.65 | 19/59 | TEC |
| | RAR-L7 | RP11-87F15-RP11-347K3 | 4q34.1-q26.33 | 177.12-189.92 | 12.79 | 10/59 | CLDN22, IRF2, ING2, CASP3 |
| | RAR-L8 | CTD-2011L22-RP11-20O13 | 5q14.3-q15 | 91.52-93.36 | 1.83 | 12/59 | |
| | RAR-L9 | RP11-391B7-CTC-279E3 | 5q33.3-q34 | 157.36-160.78 | 3.41 | 12/59 | |
| | RAR-L10 | RP3-365E2-RP1-13D10 | 6p23-p22.3 | 13.97-17.02 | 3.04 | 19/59 | |
| | RAR-L11 | RP11-338B22-RP11-16H11 | 8p23.3-p23.2 | 0.46-4.49 | 4.02 | 23/59 | |
| | RAR-L12 | RP11-325D15-RP11-619F23 | 10q22.2-q22.3 | 77.33-79.26 | 1.91 | 13/59 | |
| | RAR-L13 | RP11-381K7-RP11-426E5 | 10q25.2 | 112.7-114.46 | 1.75 | 12/59 | ACSL5 |
| | RAR-L14 | RP11-164H13-RP11-76E12 | 14q32.13-q32.2 | 95.15-97.53 | 2.40 | 28/59 | |
| | RAR-L15 | RP11-353B9-RP11-105D1 | 15q21.1-q21.2 | 47.35-49.35 | 1.99 | 17/59 | |
| | RAR-L16 | RP11-231A23-RP11-24N10 | 15q22.2-q22.31 | 57.44-61.74 | 4.29 | 21/59 | ANXA2, RORA |
| | RAR-L17 | RP11-401O9-RP11-219A15 | 17p13.1-p11.2 | 9.83-17.02 | 7.18 | 28/59 | SCO1 |
| | RAR-L18 | RP5-836L9-RP11-121A13 | 17p11.2 | 19.88-22.24 | 0.35 | 23/59 | |
| | RAR-L19 | RP1-270M7-RP1-152M24 | 21q11.2-q21.1 | 15.21-16.83 | 1.61 | 18/59 | |
| | RAR-L20 | RP11-98O13-RP5-1031P17 | 21q22.13-q22.2 | 37.50-40.67 | 3.16 | 13/59 | |

Note:
The frequency represents the number of samples with the corresponding genomic change out of 59 colorectal cancers.

Several cancer-related genes are included in the RARs. For example, known oncogenes such as MYC and REL as well as putative oncogens such as BLC11A, PLD1, ECT2, AGR2, TWIST1, and BIRC4 are included in the RAR-Gs. Also, a number of known or putative tumor suppressor genes such as CAMTA1, FAF1, CTH, PTGER3, TEC, CLDN22, ING2, IRF2, ACSL5, ANXA2, RORA, and SCO1 are located in the RAR-Ls.

Example 4

High Copy Number Changes

All high-level amplifications and homozygous deletions along with the putative cancer-related genes located in them are summarized in Table 3.

TABLE 3

Genomic segments representing high copy number changes in 59 colorectal cancers

| Change | BAC clone ID | Cytoband | Boundary (Mb) | Size (Mb) | Observed cases[a] | Putative cancer-related genes |
|---|---|---|---|---|---|---|
| Amp | RP11-449G3-RP4-725G10 | 7p12.1-p11.2 | 53.47-56.26 | 2.78 | CCRC93 | EGFR |
| | RP4-550A13-RP11-506M12 | 7q22.1 | 97.86-99.59 | 1.72 | CCRC29 | MCM7 |
| | RP11-90J7-RP11-20E23 | 10q22.3-q23.1 | 79.26-83.53 | 4.27 | CCRC37 | |
| | RP5-1096D14-RP11-319E16 | 12p13.33-p13.31 | 1.43-5.57 | 4.13 | CCRC33 | CCND2, FGF6, FGF23, AKAP3 |
| | RP11-129M14-RP11-332E3 | 13q21.31-q22.2 | 64.90-75.98 | 11.07 | CCRC59 | KLF5 |
| | RP11-564N10-RP11-255P5 | 13q33.1 | 100.86-102.84 | 1.97 | CCRC72 | FGF14 |
| | RP11-265C7-RP11-245B11 | 13q34 | 112.49-113.85 | 1.35 | CCRC19 | CUL4A, TFDP1 |
| | RP11-390P24-RP11-94L15 | 17q12-q21.2 | 34.71-35.45 | 0.73 | CCRC17, 81 | PPARBP, PPP1R1B, STARD3, TCAP, PNMT, ERBB2, GRB7, CDC6, RARA |
| | RP11-13L22-RP11-28F1 | 18q21.33 | 57.72-59.73 | 2 | CCRC80 | |
| | RP3-324O17-RP4-633O20 | 20q11.21-q11.23 | 28.92-36.34 | 7.41 | CCRC12, 90, 93 | ID1, BCL2L1, HCK, TPX2, MYLK2, PLAGL2, TGIF2, SRC |
| | RP5-1028D15-RP4-719C8 | 20q13.12-q13.33 | 41.66-58.31 | 16.64 | CCRC 11, 43, 72, 90, 93 | MYBL2, RAB22A |
| HD | RP11-350K6-RP11-520K18 | 18q21.31-q21.33 | 54.78-57.70 | 2.91 | CCRC73 | PMAIP1/NOXA |
| | RP11-25L3-RPU-396D4 | 18q22.3-q23 | 69.26-71.83 | 2.56 | CCRC73 | — |

Note:
Amp, amplification; HD, homozygous deletion.
[a] In case of more than two cases observed, the boundary of high copy number change was defined as the most extended set of clones, so they were not necessarily overlapping.

In sum, 11 genomic segments of high-level amplifications and 2 homozygous deletions were identified at least in one case. Although, most high copy number changes were identified in single case, amplifications on 17q12, 20q11 and 20q13 were observed in more than two cases. There are known oncogenes such as EGFR, CCND2, ERBB2, and MYBL2 in the amplified regions. Also, there are several putative cancer-related genes in the high copy number change regions (Table 3).

Example 5

Correlation Between Genomic Alterations

Pairwise correlation analysis between the RARs was done to investigate the significant co-occurrence of them. For comparison, all possible pairs of RARs located on different chromosomal arms were considered. Five pairs of RARs were found to be significantly correlated to each other after adjusting for multiple testing. The RAR-L5 on 4p15 correlates with the RAR-L2 on 1p33 ($r=0.66$; padj=0.0001) and the RAR-G7 on Xq24 ($r=0.51$; padj=0.042). The RAR-L17 on 17p13 correlates with the RAR-L5 on 4p15 ($r=0.56$; padj=0.0073) and the RAR-L14 on 14q32 ($r=0.59$; padj=0.0022). The RAR-L6 on 4p12 correlates with the RAR-L2 on 1p33 ($r=0.53$, padj=0.02).

We further investigated whether significantly correlated RARs share functionally related genes using public gene database, Gene Ontology (GO). We selected genes that have the same functional annotations (e.g. signal transduction) but are separately located on two correlated RARs. Three RAR pairs were found to share functionally related genes across 12 annotations.

TABLE 4

Functionally related genes shared by significantly co-occurred RARs

| Pathway | RefSeq | Symbol | RAR-G7 | RAR-L5 | RAR-L17 | RAR-L14 |
|---|---|---|---|---|---|---|
| adjusted p-value | | | 0.0428 | 0.0073 | | 0.0022 |
| Receptor activity | NM_000623 | BDKRB2 | | | | 1 |
| | NM_000676 | ADORA2B | | | 1 | |
| | NM_000710 | BDKRB1 | | | | 1 |
| | NM_001775 | CD38 | | 1 | | |
| | NM_006667 | PGRMC1 | 1 | | | |
| | NM_012452 | TNFRSF13B | | | 1 | |
| Regulation of transcription, DNA-dependent | NM_001189 | BAPX1 | | 1 | | |
| | NM_006777 | ZBTB33 | 1 | | | |

TABLE 4-continued

Functionally related genes shared by significantly co-occurred RARs

| Pathway | RefSeq | Symbol | RAR-G7 | RAR-L5 | RAR-L17 | RAR-L14 |
|---|---|---|---|---|---|---|
| | NM_017544 | NKRF | 1 | | | |
| | NM_020653 | ZNF287 | | | 1 | |
| | NM_020787 | ZNF624 | | | 1 | |
| | NM_032498 | PEPP-2 | 1 | | | |
| | NM_144680 | ZNF18 | | | 1 | |
| | NM_153604 | MYOCD | | | 1 | |
| Transcription factor activity | NM_001189 | BAPX1 | | 1 | | |
| | NM_006470 | TRIM16 | | | 1 | |
| | NM_020653 | ZNF287 | | | 1 | |
| | NM_032498 | PEPP-2 | 1 | | | |
| | NM_144680 | ZNF18 | | | 1 | |
| Sensory perception | NM_000623 | BDKRB2 | | | | 1 |
| | NM_006017 | PROM1 | | 1 | | |
| | NM_016113 | TRPV2 | | | 1 | |
| Signal transduction | NM_000676 | ADORA2B | | | 1 | |
| | NM_000710 | BDKRB1 | | | | 1 |
| | NM_001775 | CD38 | | 1 | | |
| | NM_003010 | MAP2K4 | | | 1 | |
| | NM_005130 | FGFBP1 | | 1 | | |
| | NM_016084 | RASD1 | | | 1 | |
| Development | NM_001290 | LDB2 | | 1 | | |
| | NM_004334 | BST1 | | 1 | | |
| | NM_006978 | RNF113A | 1 | | | |
| ATP binding | NM_002470 | MYH3 | | | 1 | |
| | NM_002472 | MYH8 | | | 1 | |
| | NM_003010 | MAP2K4 | | | 1 | |
| | NM_003384 | VRK1 | | | | 1 |
| | NM_003802 | MYH13 | | | 1 | |
| | NM_005963 | MYH1 | | | 1 | |
| | NM_017533 | MYH4 | | | 1 | |
| | NM_017534 | MYH2 | | | 1 | |
| Generation of precursor metabolites and energy | NM_001775 | CD38 | | 1 | | |
| | NM_004541 | NDUFA1 | 1 | | | |
| Hydrolase activity | NM_001775 | CD38 | | 1 | | |
| | NM_004278 | PIGL | | | 1 | |
| | NM_004334 | BST1 | | 1 | | |
| Protein amino acid phosphorylation | NM_003010 | MAP2K4 | | | 1 | |
| | NM_003384 | VRK1 | | | | 1 |
| G-protein coupled receptor protein signaling pathway | NM_000623 | BDKRB2 | | | | 1 |
| | NM_000676 | ADORA2B | | | 1 | |
| | NM_000710 | BDKRB1 | | | | 1 |
| | NM_016084 | RASD1 | | | 1 | |
| Transcription | NM_020653 | ZNF287 | | | 1 | |
| | NM_032632 | PAPOLA | | | | 1 |

Example 6

Differential Distribution of Genetic Alterations According to Clinicopathologic Parameters Four types of clinical variables (age, stage, sex, tumor site) were analysed for their associations with the genomic alterations identified. The RAR-G7, RAR-L11, RAR-L12, RAR-L13, RAR-L16, RAR-L17, RAR-L18, gains of 8q, 19p, X, loss of 14q, 15q, Xq, and Y were associated with sex. The RAR-G3, RAR-L1, RAR-L2, RAR-L5, RAR-L6, RAR-L20, loss of 1p, and 4p were found to be associated with advanced tumor stage. The RAR-G7, RAR-L4, RAR-L9, RAR-L11, RAR-L12, gains of 13q, 20p, 20q, losses of 18p, and 18q were associated with rectosigmoid tumor site.

Example 7

Survival Analysis with Genomic Alterations

Survival analysis was performed to assess the prognostic values of the clinicopathological parameters and the RARs. In univariate analysis, advanced stage (p=0.001), RAR-L1 (p=0.000), RAR-L4 (p=0.026), and RAR-L20 (p=0.031) were significantly associated with poor survival (FIG. 3). The statistically highest significance was observed for the existence of RAR-L1.

Figure 3A:
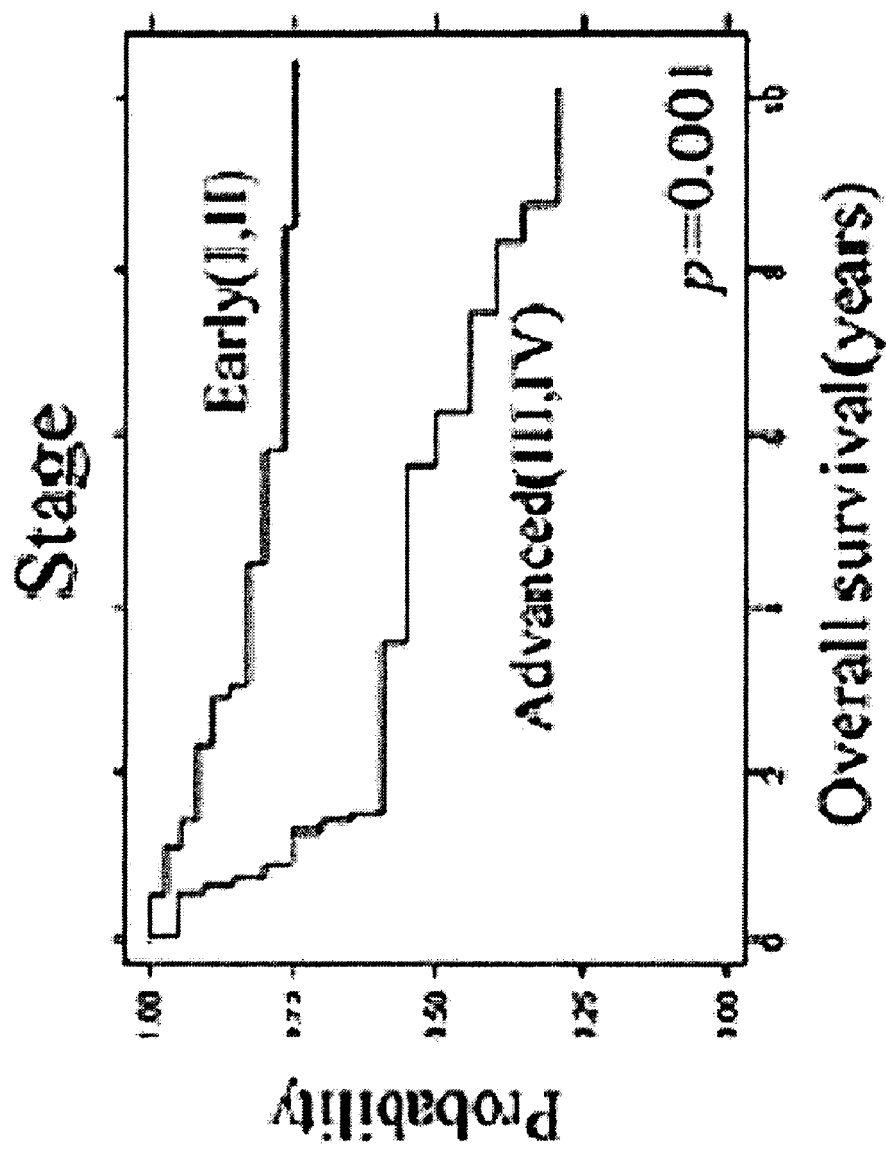
FIG. 3 shows an analysis result for examples of recurrently altered regions (RAR) and survival curves. A: Stage, B: RAR-L1 on 1p36, C: RAR-L4 on 1p31, D: RAR-L20 on 21q22, E: Graph of RAR-L1 (loss of chromosome 1p36), F: Graph of RAR-L20 (loss of chromosome 21q22).
Figure 3B:
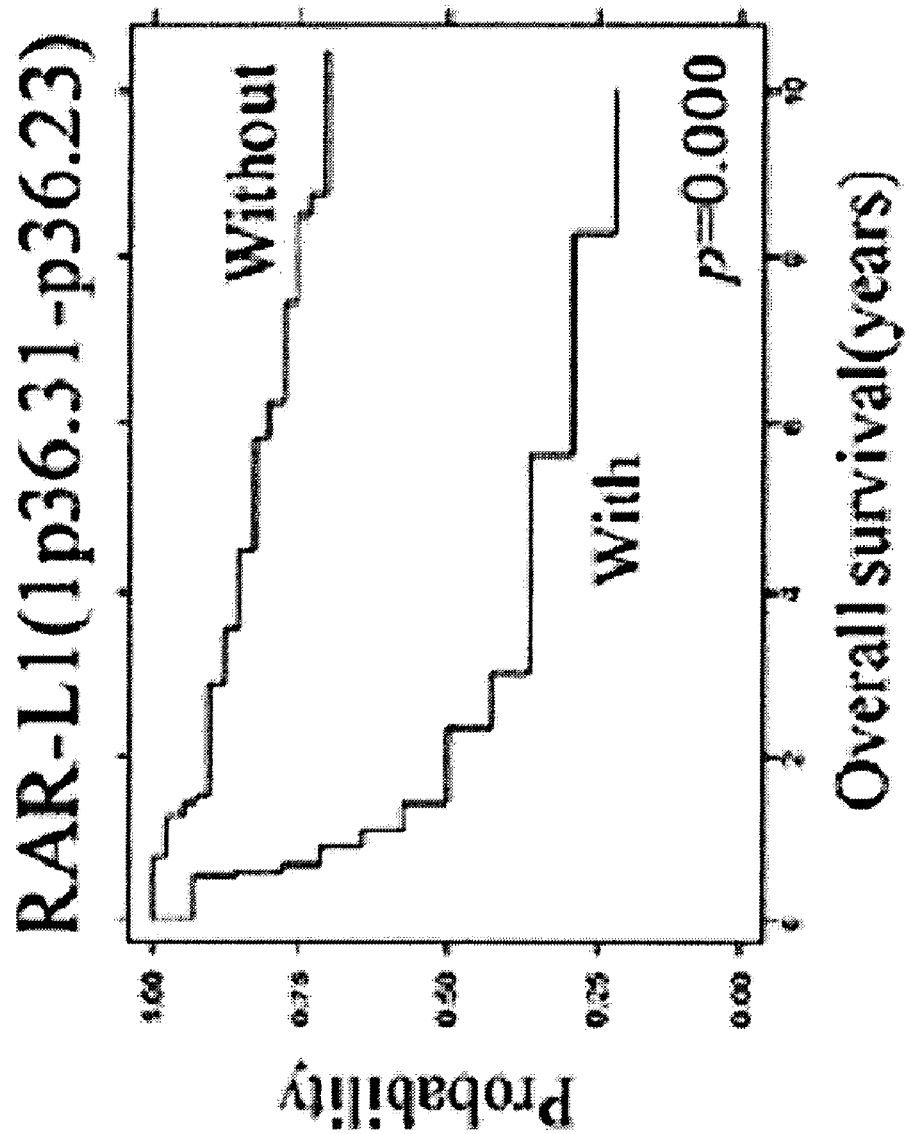
Figure 3C:
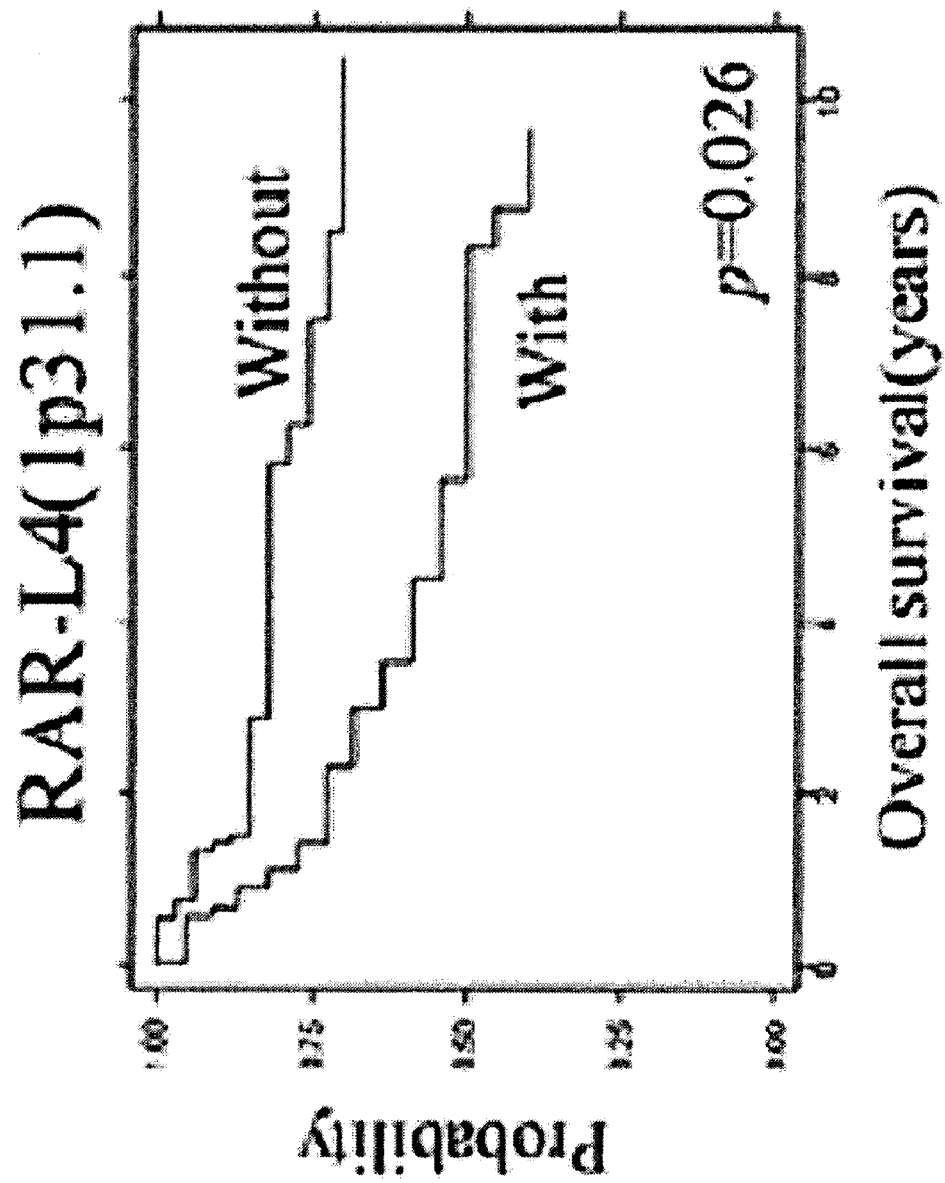
Figure 3D:
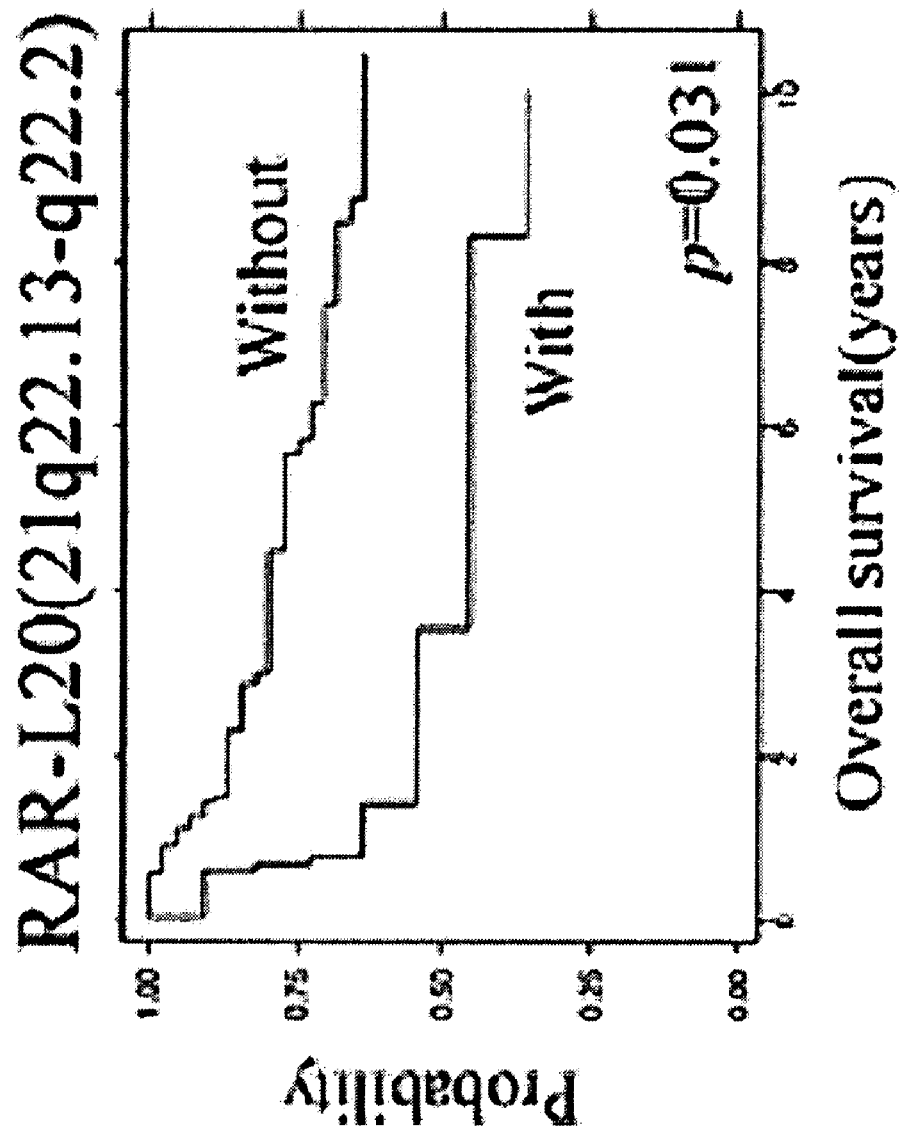
Figure 3E:
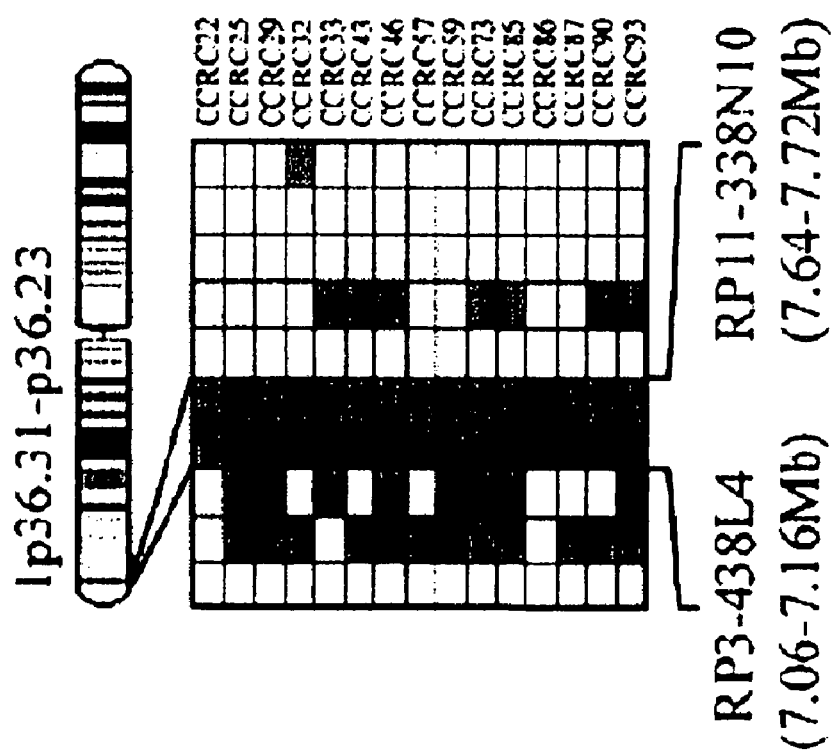
Figure 3F:
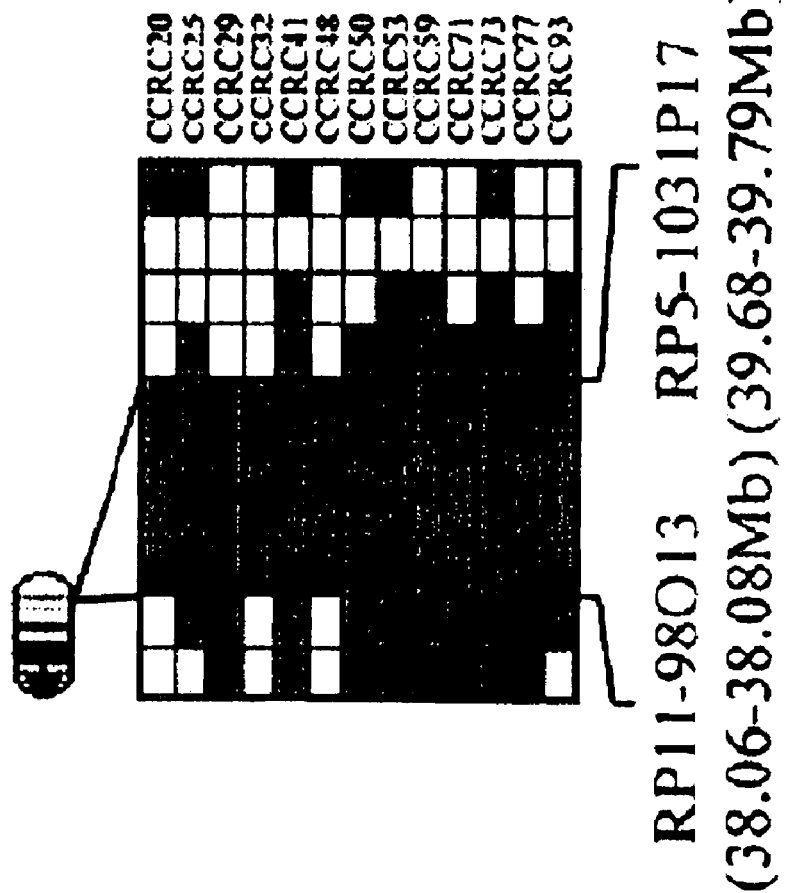

Multivariate analysis using all the significant genomic alterations identified in univariate analysis as well as clinical variables such as age, sex and stage of tumor revealed that two RARs (RAR-L1 and RAR-L20), age, and stage are independent predictors for poor outcome in CRC (Table 5). Representative diagrams of these two RARs showing significant association with patient survival are illustrated in FIGS. 3E and F.

TABLE 5

Result of Cox regression analysis

| Variable | Hazard ratio | 95% Confidence interval | | p value |
|---|---|---|---|---|
| | | Lower | Upper | |
| Age | 9.979 | 2.688 | 37.050 | 0.001 |
| Stage | 5.073 | 1.880 | 13.689 | 0.001 |
| RAR-L1 | 8.151 | 2.167 | 30.657 | 0.002 |
| RAR-L20 | 3.528 | 1.098 | 11.339 | 0.034 |
| Age | 6.455 | 2.034 | 20.488 | 0.002 |

TABLE 5-continued

Result of Cox regression analysis

| Variable | Hazard ratio | 95% Confidence interval | | p value |
| --- | --- | --- | --- | --- |
| | | Lower | Upper | |
| Stage | 7.409 | 2.481 | 22.124 | 0.000 |
| Low CAMTA1 | 7.089 | 2.121 | 23.688 | 0.001 |

Note:
upper table, Cox regression using all the significant genomic alterations identified in univariate analysis as well as clinical variables such as age, sex and stage; lower table, Cox regression using CAMTA1 expression status and clinical variables such as age, sex and stage.

Example 8

Expression of Putative Cancer-Related Gene in Survival-Associated RARs (1) Real-Time Quantitative PCR Assay The first-strand cDNA was synthesized from total RNA of 44 pairs of cancer/normal tissues and 3 cell lines (RKO, HT29 and HCT116) using M-MLV reverse transcriptase (Invitrogen, Carlsbad, Calif.). Real-time quantitative PCR for analyzing CAMTA1 expression profile was performed using Mx3000P qPCR system and MxPro Version 3.00 software (Stratagene, CA, USA). The real-time qPCR mixture of 20 µl contained 10 ng of cDNA, 1X SYBR® Green Tbr polymerase mixture (FINNZYMES, Finland), 0.5×ROX, and primers of 20 pmole. GAPDH was used as an internal control in each procedure. The thermal cycling was as follows: 10 min at 95° C. followed by 40 cycles of 10 sec at 94° C., 30 sec at 54° C. and 30 sec at 72° C. To verify specific amplification, melting curve analysis was performed (55-95° C., 0.5° C./sec). Relative quantification was performed by the ΔΔCT method. We defined 40% reduction of expression in cancer tissue as low CAMTA1 expression. All the experiments were repeated twice and mean value of intensity ratio with standard deviation was plotted for each case. Primer sequences for CAMTA1 real-time quantitative PCR were as follows: 5'-AGTGCAGAAAATGAAGAATGCG-3' (SEQ ID NO: 1) and 5'-CAAAATTCTCCTGCTTGATTCG-3' (SEQ ID NO: 2) for forward and reverse, respectively.

(2) CAMTA1 Mutation Analysis

Somatic mutation of CAMTA1 was screened by PCR-direct sequencing. Primer sets for amplification of specific exons were prepared as described previously with some modifications. All the amplification was performed using Phusion™ High-Fidelity DNA polymerase (FINNZYMES, Finland). PCR products were purified using MEGA-spin™ gel extraction kit (iNtRON, Korea).

TABLE 6

Primer sequences for CAMTA1 mutation analysis
(SEQ ID NOS 3-34,
respectively, in order of appearance)

| | Forward primer | Reverse primer |
| --- | --- | --- |
| Exon1 | CCACTAGGAAGCTTTGTTTAG GT | CTCTTACCTTCCGGCCTTGTT T |
| Exon2 | TTGGCAGGAATATCACAGAAG AG | TTTTGCTACCCCAGAAGGATT A |
| Exon3 | GGAGATTTTATCTATTATTTT CTCTA | GGACTATGTGAAGCAACCTAA |
| Exon4 | AACAGCAAAAACTTTCTTACC TCTC | CCAAATCAGGTAATCAATGCA |
| Exon5 | TTTCTTCTACTTGGTACTCTT GGTA | AATGACATTTGTGCACCAAGG |
| Exon6 | CCCTCTTTCCAACTGAATTCT C | CCAGAGACAGAAGAAGAATCC |
| Exon7 | AGTCTGCTAATATCCCACATG CGC | TGGTTGATGCCAGCCTGGTTC |
| Exon9 | CCAGCACCATGGCCTACATGC | CAGCGGCGGCAGCTTACCTCT |
| Exon10 | AACTCTGTTCCCCTCTCTGTT CTCT | CAGGCCATCACACTCACCTTG |
| Exon11 | CATTAAGGAGAGCTGGACATT A | ACGACCCAAGCACTGTTCTTA |
| Exon13 | GTGGTATGCGAGAAGATGATG | CAGTGCTCAGGAAGAATGTGA |
| Exon14 | TACCCAGTTGGGTTTCATCTT GGTG | ATGCCAGACTGGAAGAACAGC AAG |
| Exon15-1 | GGTCTTGACCTCTGATTGAGA | CTCTGCTAATTTCACATGACC |
| Exon15-2 | ATCTCGATTCCCGACTCTCTA G | ATAACAGTGACTCCCTTGGGT |
| Exon19 | AAGCTGACATTTCTGGTAGTT AATC | TTTAGCCAAACCAGGATCTTC |
| Exon20 | TTCTCTTCTTCCCTTCCCGGT A | AAGTCAGAGTTCTCTTCCCTA GGG |

Figure 4:
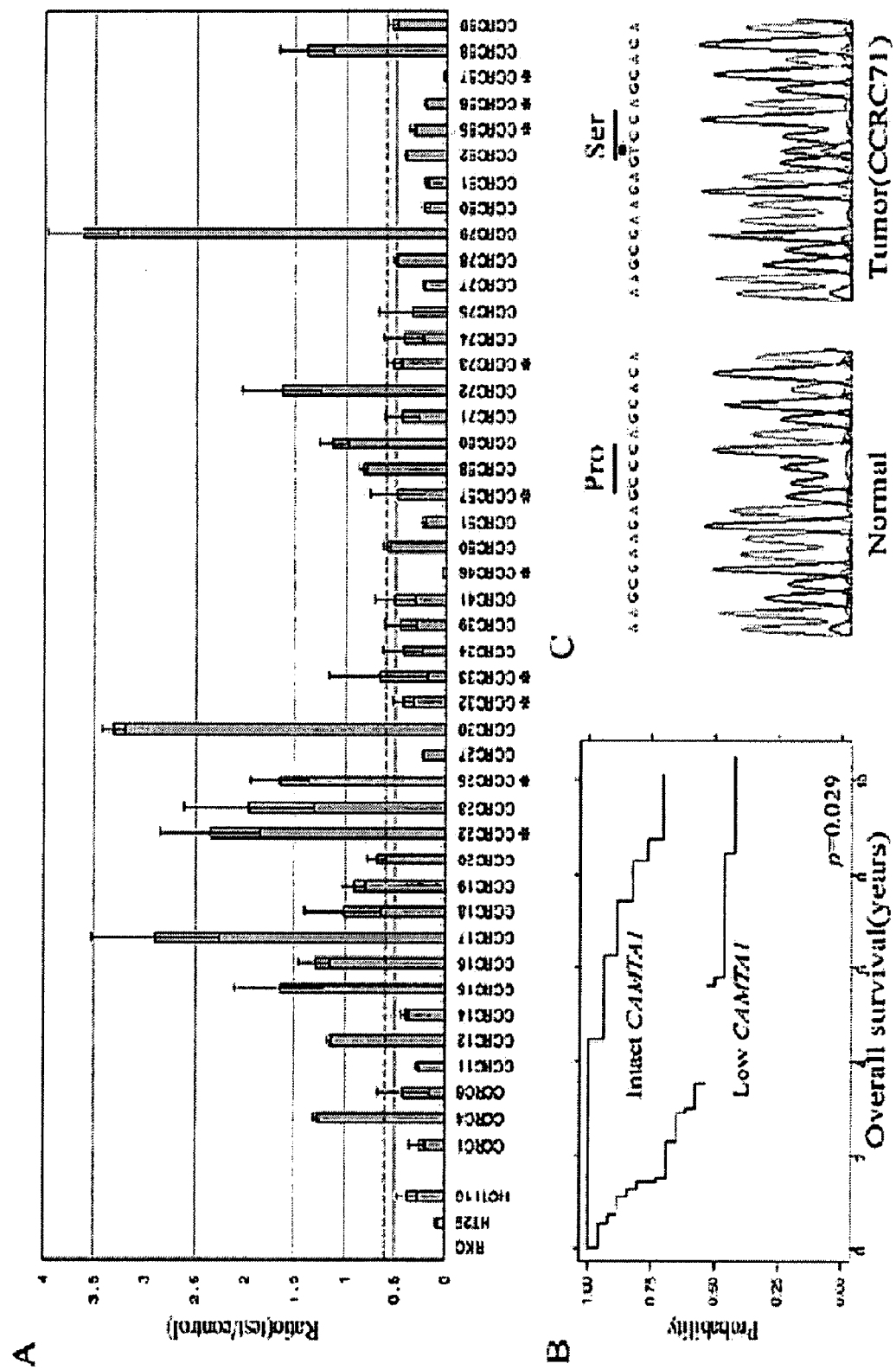
FIG. 4 shows an analysis result for expression profiles of cancer suppressor genes. A: Plots of tumor/normal intensity ratios, B: Kaplan-Meier survival curves, C: Examples of missense mutation (SEQ ID NOS 35 and 36, respectively, in order of appearance).

Among the coding genes in RAR-L1 and RAR-20, CAMTA1 was suggested as a putative tumor suppressor gene in neuronal tumor. Therefore, we examined the expression profile of this gene in three CRC cell lines and 44 pairs primary CRCs by real-time quantitative PCR. Ratio of gene expression values (cancer versus normal) was calculated. All three cell lines and 26 CRCs out of 44 (59.1%) showed low expression of CAMTA1 compared with normal tissue (FIG. 4A). Low CAMTA1 expression was significantly associated with poor survival than CAMTA1 intact cases (p=0.029) (FIG. 4B). After being adjusted for age, sex and stage by Cox regression, low CAMTA1 expression showed more significant association with poor survival as an independent predictor (HR=7.089, p=0.001) (Table 5).

Low CAMTA1 expression was observed more frequently in the CRCs with RAR-L1 (70%, 7/10) than those without RAR-L1 (55.9%, 19/34) and expression level was also lower in CRCs with RAR-L1 (mean ratio 0.74) than those without RAR-L1 (mean ratio 0.93), but not significantly. For further exploring putative mechanisms of low CAMTA1 expression, we screened somatic mutations (26 CRCs) and methylation status (38 CRCs). One missense mutation was found in a primary CRC (CCRC71), which showed low CAMTA1 expression but without RAR-L1 (FIG. 4C). However, no hypermethylation was observed in the promoter region of CAMTA1 (data not shown).

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

All patents and publications mentioned in this specification are herein incorporated by reference to the same extent as if each independent patent and publication was specifically and individually indicated to be incorporated by reference.

REFERENCES

1. Parkin D M, Bray F, Ferlay J, Pisani P. Global cancer statistics, 2002. CA Cancer J Clin 2005; 55:74-108.
2. National Statistical Office, Korea. Korean Statistical Information System. 2006. Available from: URL: ncc.re.kr.
3. Shin H R, Won Y J, Jung K W, Kong H J, Yim S H, Lee J K, Noh H I, Lee J K, Park J G. Nationwide Cancer Incidence in Korea, 1999-2001; First result using the National Cancer Incidence Database. Cancer Res Treat 2006; 37:in press.
4. Michor F, Iwasa Y, Lengauer C, Nowak M A. Dynamics of colorectal cancer. Semin Cancer Biol 2005; 15:484-493.
5. Yim S H, Chung Y J. Current Status and Future Clinical Applications of Array based Comparative Genomic Hybridization. Genomics & Informatics 2004; 2:113-120.
6. Pinkel D, Segraves R, Sudar D, Clark S, Poole I, Kowbel D, Collins C, Kuo W L, Chen C, Zhai Y, Dairkee S H, Ljung B M, Gray J W, Albertson D G. High resolution analysis of DNA copy number variation using comparative genomic hybridization to microarrays. Nat Genet 1998; 20:207-211.
7. Fiegler H, Carr P, Douglas E J, Burford D C, Hunt S, Scott C E, Smith J, Vetrie D, Gorman P, Tomlinson I P, Carter N P. DNA microarrays for comparative genomic hybridization based on DOP-PCR amplification of BAC and PAC clones. Genes Chromosomes Cancer 2003; 36:361-374.
8. Kim T M, Yim S H, Lee J S, Kwon M S, Ryu J W, Kang H M, Fiegler H, Carter N P, Chung Y J. Genome-wide screening of genomic alterations and their clinicopathologic implications in non-small cell lung cancers. Clin Cancer Res 2005; 11:8235-8242.
9. Chung Y J, Jonkers J, Kitson H, Fiegler H, Humphray S, Scott C, Hunt S, Yu Y, Nishijima I, Velds A, Holstege H, Carter N, Bradley A. A whole-genome mouse BAC microarray with 1-Mb resolution for analysis of DNA copy number changes by array comparative genomic hybridization. Genome Res 2004; 14:188-196.
10. Kim S Y, Nam S W, Lee S H, Park W S, Yoo N J, Lee J Y, Chung Y J. ArrayCyGHt: a web application for analysis and visualization of array-CGH data. Bioinformatics 2005; 21:2554-2555.
11. Livak K J, Schmittgen T D. Analysis of relative gene expression data using real-time quantitative PCR and the 2 (-Delta Delta C(T)) Method. Methods 2001; 25: 402-408.
12. Henrich K O, Fischer M, Mertens D, Benner A, Wiedemeyer R, Brors B, Oberthuer A, Berthold F, Wei J S, Khan J, Schwab M, Westermann F. Reduced expression of CAMTA1 correlates with adverse outcome in neuroblastoma patients. Clin Cancer Res 2006; 12:131-138.
13. Barbashina V, Salazar P, Holland E C, Rosenblum M K, Ladanyi M. Allelic losses at 1p36 and 19q13 in gliomas: correlation with histologic classification, definition of a 150-kb minimal deleted region on 1p36, and evaluation of CAMTA1 as a candidate tumor suppressor gene. Clin Cancer Res 2005; 11:1119-1128.
14. Schouten J P, McElgunn C J, Waaijer R, Zwijnenburg D, Diepvens F, Pals G. Relative quantification of 40 nucleic acid sequences by multiplex ligation-dependent probe amplification. Nucleic Acids Res 2002; 30:e57.
15. He Q J, Zeng W F, Sham J S, Xie D, Yang X W, Lin H L, Zhan W H, Lin F, Zeng S D, Nie D, Ma L F, Li C J, Lu S, Guan X Y. Recurrent genetic alterations in 26 colorectal carcinomas and 21 adenomas from Chinese patients. Cancer Genet Cytogenet 2003; 144:112-118.
16. Poeaim S, Rerkamnuaychoke B, Jesdapatarakul S, Campiranon A. Chromosome alterations in colorectal cancer in That patients. Cancer Genet Cytogenet 2005; 160:152-159.
17. Ried T, Knutzen R, Steinbeck R, Blegen H, Schrock E, Heselmeyer K, du Manoir S, Auer G. Comparative genomic hybridization reveals a specific pattern of chromosomal gains and losses during the genesis of colorectal tumors. Genes Chromosomes Cancer 1996; 15:234-245.
18. Nakao K, Mehta K R, Fridlyand J, Moore D H, Jain A N, Lafuente A, Wiencke J W, Terdiman J P, Waldman F M. High-resolution analysis of DNA copy number alterations in colorectal cancer by array-based comparative genomic hybridization. Carcinogenesis 2004; 25:1345-1357.
19. Knosel T, Petersen S, Schwabe H, Schluns K, Stein U, Schlag P M, Dietel M, Petersen I. Incidence of chromosomal imbalances in advanced colorectal carcinomas and their metastases. Virchows Arch 2002; 440:187-194.
20. Jones A M, Douglas E J, Halford S E, Fiegler H, Gorman P A, Roylance R R, Carter N P, Tomlinson I P. Array-CGH analysis of microsatellite-stable, near-diploid bowel cancers and comparison with other types of colorectal carcinoma. Oncogene 2005; 24:118-129.
21. Knosel T, Schluns K, Stein U, Schwabe H, Schlag P M, Dietel M, Petersen I. Genetic imbalances with impact on survival in colorectal cancer patients. Histopathology 2003; 43:323-331.
22. Aragane H, Sakakura C, Nakanishi M, Yasuoka R, Fujita Y, Taniguchi H, Hagiwara A, Yamaguchi T, Abe T, Inazawa J, Yamagishi H. Chromosomal aberrations in colorectal cancers and liver metastases analyzed by comparative genomic hybridization. Int J Cancer 2001; 94:623-629.
23. Douglas E J, Fiegler H, Rowan A, Halford S, Bicknell D C, Bodmer W, Tomlinson I P, Carter N P. Array comparative genomic hybridization analysis of colorectal cancer cell lines and primary carcinomas. Cancer Res 2004; 64:4817-4825.
24. De Angelis P M, Clausen O P, Schjolberg A, Stokke T. Chromosomal gains and losses in primary colorectal carcinomas detected by CGH and their associations with tumour DNA ploidy, genotypes and phenotypes. Br J Cancer 1999; 80:526-535.
25. Shivapurkar N, Maitra A, Milchgrub S, Gazdar A F. Deletions of chromosome 4 occur early during the pathogenesis of colorectal carcinoma. Hum Pathol 2001; 32:169-177.
26. Finch R, Moore H G, Lindor N, Jalal S M, Markowitz A, Suresh J, Offit K, Guillem J G. Familial adenomatous polyposis and mental retardation caused by a de novo chromosomal deletion at 5q15-q22: report of a case. Dis Colon Rectum 2005; 48:2148-2152.
27. Flanagan J M, Healey S, Young J, Whitehall V, Trott D A, Newbold R F, Chenevix-Trench G. Mapping of a candidate colorectal cancer tumor-suppressor gene to a 900-kilobase region on the short arm of chromosome 8. Genes Chromosomes Cancer 2004; 40:247-260.
28. Frayling I M, Bodmer W F, Tomlinson I P. Allele loss in colorectal cancer at the Cowden disease/juvenile polyposis locus on 10q. Cancer Genet Cytogenet 1997; 97:64-69.
29. Bando T, Kato Y, Ihara Y, Yamagishi F, Tsukada K, Isobe M. Loss of heterozygosity of 14q32 in colorectal carcinoma. Cancer Genet Cytogenet 1999; 111:161-165.
30. Park W S, Park J Y, Oh R R, Yoo N J, Lee S H, Shin M S, Lee H K, Han S, Yoon S K, Kim S Y, Choi C, Kim P J, Oh S T, Lee J Y. A distinct tumor suppressor gene locus on chromosome 15q21.1 in sporadic form of colorectal cancer. Cancer Res 2000; 60:70-73.
31. Risio M, Casorzo L, Chiecchio L, De Rosa G, Rossini F P. Deletions of 17p are associated with transition from early to advanced colorectal cancer. Cancer Genet Cytogenet 2003; 147:44-49.
32. Knosel T, Petersen S, Schwabe H, Schluns K, Stein U, Schlag P M, Dietel M, Petersen I. Incidence of chromosomal imbalances in advanced colorectal carcinomas and their metastases. Virchows Arch 2002; 440:187-194.
33. Donzelli M, Bernardi R, Negri C, Prosperi E, Padovan L, Lavialle C, Brison O, Scovassi A I. Apoptosis-prone phenotype of human colon carcinoma cells with a high level amplification of the c-myc gene. Oncogene 1999; 18:439-448.
34. Lakshman M, Subramaniam V, Rubenthiran U, Jothy S. CD44 promotes resistance to apoptosis in human colon cancer cells. Exp Mol Pathol 2004; 77:18-25.
35. Cummins J M, Kohli M, Rago C, Kinzler K W, Vogelstein B, Bunz F. X-linked inhibitor of apoptosis protein (XIAP) is a nonredundant modulator of tumor necrosis factor-related apoptosis-inducing ligand (TRAIL)-mediated apoptosis in human cancer cells. Cancer Res 2004; 64:3006-3008.
36. Satterwhite E, Sonoki T, Willis T G, Harder L, Nowak R, Arriola E L, Liu H, Price H P, Gesk S, Steinemann D, Schlegelberger B, Oscier D G, Siebert R, Tucker P W, Dyer M J. The BCL11 gene family: involvement of BCL11A in lymphoid malignancies. Blood 2001; 98:3413-3420.
37. Ahn B H, Kim S Y, Kim E H, Choi K S, Kwon T K, Lee Y H, Chang J S, Kim M S, Jo Y H, Min D S. Transmodulation between phospholipase D and c-Src enhances cell proliferation. Mol Cell Biol 2003; 23:3103-3115.
38. Zhang J S, Gong A, Cheville J C, Smith D I, Young C Y. AGR2, an androgen-inducible secretory protein overexpressed in prostate cancer. Genes Chromosomes Cancer 2005; 43:249-259.
39. Shoji Y, Takahashi M, Kitamura T, Watanabe K, Kawamori T, Maruyama T, Sugimoto Y, Negishi M, Narumiya S, Sugimura T, Wakabayashi K. Downregulation of prostaglandin E receptor subtype EP3 during colon cancer development. Gut 2004; 53:1151-1158.
40. Bjorling-Poulsen M, Seitz G, Guerra B, Issinger O G. The pro-apoptotic FAS-associated factor 1 is specifically reduced in human gastric carcinomas. Int J Oncol 2003; 23:1015-1023.
41. Dunn J R, Risk J M, Langan J E, Marlee D, Ellis A, Campbell F, Watson A J, Field J K. Physical and transcript map of the minimally deleted region III on 17p implicated in the early development of Barrett's oesophageal adenocarcinoma. Oncogene 2003; 22:4134-4142.
42. Kuo T, Fisher G A. Current status of small-molecule tyrosine kinase inhibitors targeting epidermal growth factor receptor in colorectal cancer. Clin Colorectal Cancer 2005; Suppl 2:S62-70.
43. Gunther K, Leier J, Henning G, Dimmler A, Weissbach R, Hohenberger W, Forster R. Prediction of lymph node metastasis in colorectal carcinoma by expression of chemokine receptor CCR7. Int J Cancer 2005; 116:726-733.
44. Aligayer H, Boyd D D, Heiss M M, Abdalla E K, Curley S A, Gallick G E. Activation of Src kinase in primary colorectal carcinoma: an indicator of poor clinical prognosis. Cancer 2002; 94:344-351.
45. Villunger A, Michalak E M, Coultas L, Mullauer F, Bock G, Ausserlechner M J, Adams J M, Strasser A. p53- and drug-induced apoptotic responses mediated by BH3-only proteins puma and noxa. Science 2003; 302:1036-1038.
46. Ogunbiyi O A, Goodfellow P J, Gagliardi G, Swanson P E, Birnbaum E H, Fleshman J W, Kodner I J, Moley J F. Prognostic value of chromosome 1p allelic loss in colon cancer. Gastroenterology 1997; 113:761-766.
47. Ray R, Cabal-Manzano R, Moser A R, Waldman T, Zipper L M, Aigner A, Byers S W, Riegel A T, Wellstein A. Upregulation of fibroblast growth factor-binding protein, by beta-catenin during colon carcinogenesis. Cancer Res 2003; 63:8085-8089.

What is claimed is:

1. A diagnostic method for prognostic assessment of colorectal cancer, comprising the steps of:
    (a) obtaining a nucleic acid sample from a colon tissue sample obtained from a human subject;
    (b) identifying a recurrently altered region (RAR) on a chromosome in said nucleic acid sample by array CGH;
    (c) detecting variation of expression of a specific gene in the RAR in said nucleic acid sample; and
    (d) performing prognostic assessment of colorectal cancer in the human subject based on the detected variation, wherein loss of a recurrently altered region (RAR) in step (b) and a reduced expression level of the specific gene compared to a reference from normal colon tissue indicates a poor prognosis of colorectal cancer; wherein the RAR in step (b) is the chromosome region 1p36.31-1p36.23; wherein the specific gene in step (c) is CAMTA1; and wherein poor prognosis of colorectal cancer is defined by poor survival time.

2. The diagnostic method according to claim 1, wherein the reference is obtained from a human subject not having colorectal cancer.

* * * * *

SEQUENCE LISTING

```
<160> NUMBER OF SEQ ID NOS: 36

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agtgcagaaa atgaagaatg cg                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caaaattctc ctgcttgatt cg                                              22
```

-continued

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccactaggaa gctttgttta ggt                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcttacctt ccggcttgtt t                                                21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttggcaggaa tatcacagaa gag                                              23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttttgctacc ccagaaggat ta                                               22

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggagatttta tctattattt tctcta                                           26

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggactatgtg aagcaaccta a                                                21

<210> SEQ ID NO 9
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aacagcaaaa actttcttac ctctc                                          25

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccaaatcagg taatcaatgc a                                              21

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttcttctac ttggtactct tggta                                          25

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatgacattt gtgcaccaag g                                              21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccctctttcc aactgaattc tc                                             22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagagacag aagaagaatc c                                              21

<210> SEQ ID NO 15
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
agtctgctaa tatcccacat gcgc                                              24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggttgatgc cagcctggtt c                                                 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccagcaccat ggcctacatg c                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagcggcggc agcttacctc t                                                 21

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aactctgttc ccctctctgt tctct                                             25

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caggccatca cactcacctt g                                                 21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 21
cattaaggag agctggacat ta                                          22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgacccaag cactgttctt a                                           21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtggtatgcg agaagatgat g                                           21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagtgctcag gaagaatgtg a                                           21

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tacccagttg ggtttcatct tggtg                                       25

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atgccagact ggaagaacag caag                                        24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtcttgacc tctgattgag a    21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctctgctaat ttcacatgac c    21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atctcgattc ccgactctct ag    22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ataacagtga ctcccttggg t    21

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagctgacat ttctggtagt taatc    25

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tttagccaaa ccaggatctt c    21

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ttctcttctt cccttcccgg ta                                              22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aagtcagagt tctcttccct aggg                                            24

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aagcgaagag cccagcaca                                                  19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aagcgaagag tccagcaca                                                  19
```